United States Patent
Helmstetter et al.

(10) Patent No.: US 6,867,040 B2
(45) Date of Patent: Mar. 15, 2005

(54) BIOREACTOR AND METHODS FOR PRODUCING SYNCHRONOUS CELLS

(76) Inventors: Charles E. Helmstetter, 854 Hawksbill Island Dr., Satellite Beach, FL (US) 32937; Maureen Thornton, 2660 State St., Melbourne, FL (US) 32904; Steve Gonda, 1523 Almond Brook La., Houston, TX (US) 77082

(*) Notice: Subject to any disclaimer, the term of this patent is extended or adjusted under 35 U.S.C. 154(b) by 0 days.

(21) Appl. No.: 10/373,130

(22) Filed: Feb. 24, 2003

(65) Prior Publication Data

US 2003/0129742 A1 Jul. 10, 2003

Related U.S. Application Data

(63) Continuation-in-part of application No. 10/080,333, filed on Feb. 21, 2002.
(60) Provisional application No. 60/273,775, filed on Mar. 2, 2001.

(51) Int. Cl.[7] .................................................. C12N 3/00
(52) U.S. Cl. ........................ 435/376; 435/372; 435/395; 435/401; 435/402; 435/297.2; 435/297.3; 435/298.2
(58) Field of Search ........................... 435/297.2, 297.3, 435/298.2, 376, 372, 395, 401, 402

(56) References Cited

U.S. PATENT DOCUMENTS

| | | | |
|---|---|---|---|
| 3,871,955 A | 3/1975 | Klevecz | 195/1.8 |
| 5,153,131 A | 10/1992 | Wolf et al. | 435/240.24 |
| 5,637,477 A | 6/1997 | Spaulding et al. | 435/69.1 |
| 5,851,816 A | 12/1998 | Goodwin et al. | 435/240.2 |
| 5,856,112 A | 1/1999 | Marley et al. | 435/7.23 |
| 5,962,324 A | 10/1999 | O'Connor et al. | 435/394 |
| 6,001,642 A | 12/1999 | Tsao | 435/297.3 |
| 6,261,803 B1 | 7/2001 | Zander et al. | 435/69.1 |
| 6,607,910 B1 * | 8/2003 | Dimitrijevich et al. | 435/297.1 |
| 2002/0081727 A1 * | 6/2002 | Liu | 435/395 |

OTHER PUBLICATIONS

Morphologic Differentiation of Colon Carcinoma Cell Lines HT–29 and HT–29KM in Rotating–Wall Vessels in in Vitro Cell Div. Biol., vol. 28A, pp. 47–60, Jan., 1992 by T. Goodwin, et al.

"Improved Bacterial Baby Machine: Application to *Escherichia coli* K–12" in Journal of Bacteriology, vol. 174, No. 11, pp. 3445–3449, Jun., 1992 by C. Helmstetter, et al.

"Description of a Baby Machine for *Saccharomyces cerevisiae*" in The New Biologist, vol. 3, No. 11, pp. 1089–1096, Nov., 1991 by C. Helmstetter.

"Gravity and the orientation of cell division" in Proc. Natl. Acad. Sci. USA, vol. 94, pp. 10195–10196, Sep., 1997 by C. Helmstetter.

"Preferential Release of One Daughter Cell During Division of Immobilized Chinese Hamster Ovary Cells" in Biotechnology and Bioengineering, vol. 45, pp. 374–378, 1995 by C. Helmstetter.

Charles E. Helmstetter, et al.; "Synchrony in Human, Mouse and Bacterial Cell Cultures" in Landes Bioscience; Jan./Feb. 2003; (pp. 42–45).

Maureen Thornton, et al.; "Production of Minimally Disturbed Synchronous Cultures of Hematopoietic Cells" in BioTechniques; May 2002; (pp. 1098–1105).

\* cited by examiner

*Primary Examiner*—David A. Redding
(74) *Attorney, Agent, or Firm*—Polsinelli Shalton Welte Suelthaus PC

(57) ABSTRACT

Apparatus and methods are directed to a perfusion culture system in which a rotating bioreactor is used to grow cells in a liquid culture medium, while these cells are attached to an adhesive-treated porous surface. As a result of this arrangement and its rotation, the attached cells divide, with one cell remaining attached to the substrate, while the other cell, a newborn cell is released. These newborn cells are of approximately the same age, that are collected upon leaving the bioreactor. The populations of newborn cells collected are of synchronous and are minimally, if at all, disturbed metabolically.

57 Claims, 2 Drawing Sheets

BIOREACTOR AND METHODS FOR PRODUCING SYNCHRONOUS CELLS

CROSS-REFERENCES TO RELATED APPLICATIONS

This application is a continuation in part application of U.S. patent application Ser. No. 10/080,333, entitled: METHOD FOR PRODUCING SYNCHRONOUS CELLS AND THE RESULTANT CELLS, filed on Feb. 21, 2002, which is based on U.S. Provisional Patent Application Ser. No. 60/273,775, entitled: METHOD FOR PRODUCING SYNCHRONOUS CELLS AND THE RESULTANT CELLS, filed on Mar. 2, 2001, both of these applications incorporated by reference herein.

GOVERNMENT SUPPORT

Support for the invention disclosed herein is from the National Aeronautics and Space Administration (NASA) NAG8-1582 "New Cell Culture Technology" and NASA NAG2-1508 "Gravitational Impacts On The Cell Cycle".

TECHNICAL FIELD

The present invention relates to apparatus and methods for producing synchronous cells and in particular newborn cells of a uniform culture, and in particular, a rotating bioreactor apparatus that grows cells in liquid culture media.

BACKGROUND

Thousands of biological research and development facilities worldwide deal with some aspect of the growth and division of cells. Suspensions of minimally disturbed newborn cells are valuable for analysis of the cell cycle, including analysis of all mammalian cell types. The newborn cell suspensions can be used to analyze cell cycle gene expression in mammalian cells, such as hematopoietic cells. Growing and dividing cells are used in basic research, drug development and testing, and bio-product manufacturing, for example.

Furthermore, during the past few years there has been a significant expansion in research in the related areas of cell cycle regulation, cell senescence, apoptosis, and cellular differentiation. Studies related to these specific areas require access to, and reliable production of, large quantities of cells that are at a specific, known phase of growth and division, such as a particular stage in the cell cycle, and state of senescence.

Obtaining adequate quantities of synchronous cells whose physiology is minimally disturbed, is not an easy task. This is because contemporary production methods expose cells to metabolic disturbances, such as with the addition of drugs or deprivation of nutrients, in order to obtain an exponentially growing culture of cells, where the population is distributed throughout all phases of the cell cycle, to become growth inhibited at a particular stage in the cell cycle. Even if these methods are successful, it is unclear if these cellular events represent the true "steady state" of the cells, where all biochemical and metabolic processes are in balance or an artifact created by the disturbance.

Attempts have been made to produce devices and methods for manufacturing large quantities of cells that are at specific stages in cell cycles and senescence. For example, U.S. Pat. No. 6,001,642 (Tsao) and U.S. Pat. No. 5,153,131 (Wolf) are directed to bioreactors that grow cells in suspension or are attached to a substrate for three-dimensional tissue or organ growth. However, while these devices generated cells, they did not generate newborn cells and could not continuously generate cells.

SUMMARY

The present invention is directed to systems, apparatus and methods for producing newborn cells from a culture in continuous steady-state growth. Additionally, these newborn cells are produced continuously, automatically and under simulated microgravity conditions. The apparatus is directed to a perfusion culture system in which a rotating bioreactor is used to grow cells in a liquid culture medium. Within this bioreactor, these cells are attached to an adhesive-treated porous surface, that is continuously perfused with culture medium. This attachment allows cells to divide, with one of the cells remaining bound to the porous surface while the other newborn cell moves toward a collection device. The cell that remains has not been changed metabolically, and can continue to divide and produce newborn cells. This results in cell populations of the same age being collected and the populations of these newborn cells collected are of synchronous and not disturbed metabolically.

Additionally, the rotation is typically performed at speeds that subject the cells to averaging of the gravity vector (or simulated microgravity conditions). This rotation, coupled with the continuous perfusion of culture medium on the porous surface, allows the attached cells to divide, releasing newborn cells, that are collected upon leaving the bioreactor. The cells produced in accordance with the invention can be analyzed to determine gravitational impacts on cell growth, the cell cycle, cell differentiation and cell aging. Also, the cells produced could be particularly useful in cancer or aging research, as well as studies of the effects of gravity on cells.

There is disclosed apparatus for producing synchronous cells having a vessel configured for being rotated and a substrate configured for rotating with the vessel, the substrate configured for holding cells while rotating with the vessel. There is also a system for perfusing the substrate with at least one culture medium. This perfusion is typically continuous while the substrate is rotating.

There is disclosed an embodiment of a method (process) for producing synchronous cells. This method includes providing a bioreactor having a substrate configured for holding cells and rotating in the bioreactor, holding the cells at least proximate to said substrate, rotating the substrate, and perfusing the substrate with at least one culture medium.

There is disclosed another embodiment of a method (process) for producing synchronous cells. This method includes providing a bioreactor having a vessel configured for being rotated; and a substrate for holding cells. The substrate is configured for rotating with the vessel. Cells are then attached to the substrate; and the vessel is rotated to rotate the substrate.

BRIEF DESCRIPTION OF THE DRAWINGS

Attention is now directed to the drawings, where like numerals and characters indicate like or corresponding components. In the drawings.

DETAILED DESCRIPTION OF THE DRAWINGS

Figure 1:
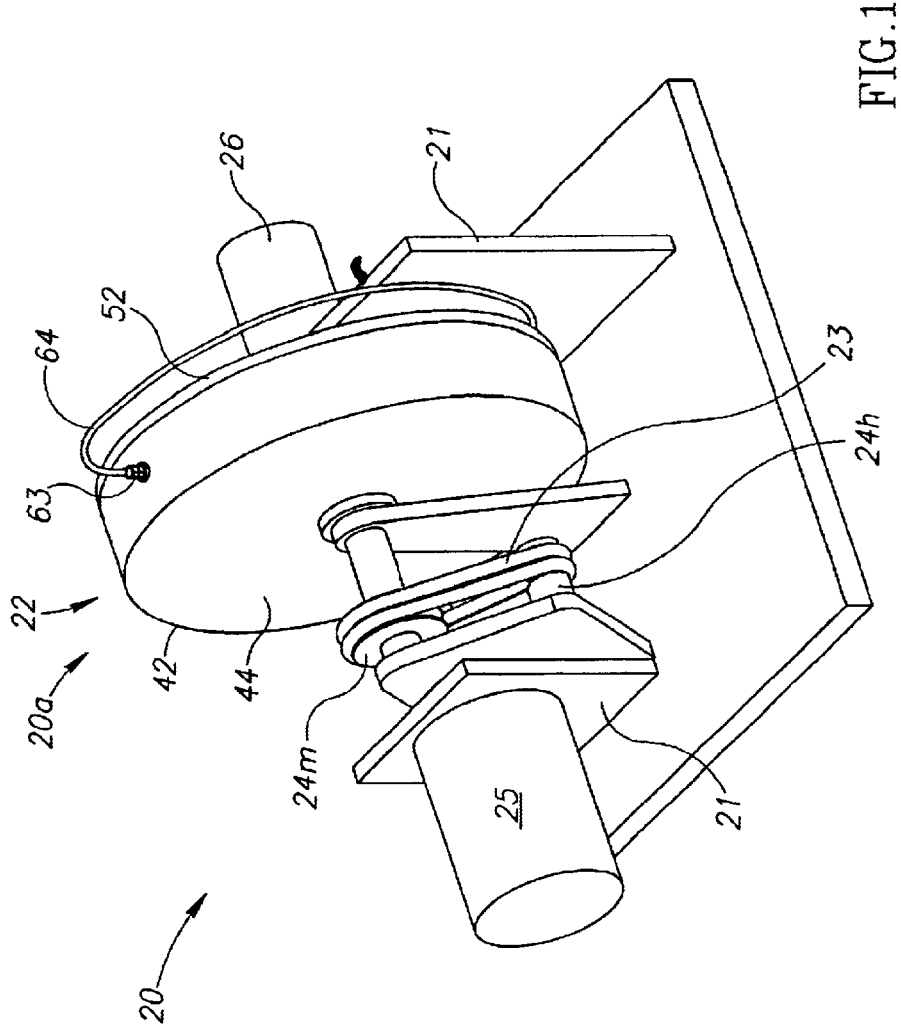
FIG. 1 is a perspective view of an embodiment of the invention.

FIG. 1 shows an embodiment of the system 20. The system 20, includes an apparatus 20a, that includes a frame 21 that supports a bioreactor 22, rotated by a drive system, typically formed of a belt drive 23 and pulleys 24h, 24m, coupled with a motor 25 and regulator (not shown). Also included is a fluid coupler 26, coupled to a rotatable neck 27 and reservoir 28 or fluid source, respectively. The fluid coupler 26 has an exit port 30, that typically empties into a collection flask 32.

An axle 40, having ends 41a, 41b, rotated by the motor 25, provides rotation to the bioreactor 22. A first end 41a of the axle 40 connects to the housing pulley 24h, while the second end 41b connects to the bioreactor 22, typically at the vessel 42. The axle 40 and rotatable neck 27 are typically coaxial, along a horizontal axis H.

The bioreactor 22 is formed from the vessel 42, including an outer shell 44 and a culture chamber 45, a porous substrate 46, for example, a membrane, a spacer 50, and a plate 52, typically with a flat surface 53. These elements are typically in a concentric alignment, and are typically substantially perpendicular to the axle 40 and the neck 27 and substantially parallel to each other. The vessel 42 typically clamps to the plate 52 by bolts 54 (of stainless steel or the like) holding the substrate and spacer 50 in place. The vessel 42, closed by the plate 52, defines an effluent chamber 56 in its interior. The rotation of the axle 40 and neck 27 (as rotated by the drive system), typically rotates the bioreactor 22 (vessel 42 and substrate 46 and other interior components) at speeds that will average the gravity vector on the cells. These rotational speeds may be between approximately 10 rpm to approximately 50 rpm, and for example, may be approximately 14 rpm, to average the gravity vector on the cells, as detailed below.

The vessel 42 is typically formed such that the outer shell 44 and the culture chamber 45 are an integral member. However, the outer shell 44 and culture chamber 45 can be separate pieces joined together by numerous known techniques and fasteners. This culture chamber 45 is typically recessed and cylindrical in shape, for holding culture medium or the like. The vessel 42 includes a single access port 63 or ports, that receive a line 64, through which culture medium is supplied to the culture chamber 45 from the reservoir 28 (as detailed below). The vessel 42 can also be disposable if desired.

The vessel 42 is typically made of plastic, stainless steel or other sterilizable material. The culture chamber 45 can also be lined with plastic or other sterilizable material. When separate pieces, the outer shell 44 and culture chamber 45 are typically made of plastic, stainless steel or any other sterilizable material. This culture chamber 45 typically is recessed (to a depth "d") so as to be formed of rigid walls and configured to have a high vertical diameter "V". This vertical diameter "V" is larger than the depth "d" to yield maximum quantities of newborn cells, for example, approximately 20 to approximately 30 times larger.

The access port 63 or ports can be any type of port used with culture or reaction vessels. This includes valves and membranes that can be penetrated by tubing, syringe, pipette or any other sampling devices.

The substrate 46 is typically a porous membrane that typically accommodates adhesive along its outer surface 68, to allow cells to attach to this surface 68. This membrane can be, for example, a 0.22 micron pore-size nitrocellulose filter manufactured by Millipore. While the substrate 46 is typically non-rigid, rigid materials are also suitable, provided that they will bind with adhesives used to attach the cells (as detailed below). The adhesives used are such that they hold cells to the substrate 46, allowing these cells to grow and divide without damaging them. The adhesives can include any composition that binds to a cell surface and can be anchored or attached to the substrate 46. Exemplary adhesives include proteins, which bind to the specific cell surface receptors, such as lectins (or lectin based compositions) that bind cell surface components, such as Concanavalin A, charged molecules (or charged molecule based compositions), that bind to cell surfaces, such as poly-D-lysine, antibodies (or antibody based compositions) (e.g., antibodies to cell surface components), other adhesives, such as fibronectin (fibronectin based compositions), as well as other substances and compositions that when placed onto the substrate 46 will bind and/or provide binding sites for the cells thereto.

The spacer 50 is typically a thin member placed into contact with the plate 52. This spacer 50 creates a uniform space between the cells 66 attached to the substrate 46 and the plate 52, so that newborn cells can move out of the port 70 in the plate 52 rapidly, without getting caught in crevices and the like. The spacer 50 is for example, a DACRON® mesh, approximately 0.2 mm thick and having openings of about 1 square millimeter each. This results in the volume of medium between the attached cells 66 and the flat plate 52 being typically not more than approximately 2.0 milliliters (ml). The space between the substrate 46 should be as small as possible to enable released newborn cells to exit the bioreactor 22 as soon as they have been produced. This space is typically approximately 0.1 mm to approximately 0.2 mm.

In alternate embodiments, use of the spacer 50 is optional, and typically spacers are not employed at all. Rather, in these alternate embodiments, a rigid substrate 46 is used, and coupled with the rigidity of the plate 52, the approximately 0.1 mm to approximately 0.2 mm gap is uniformly maintained between the cells 66 and the plate 52, eliminating the need for the spacer 50.

The plate 52 includes a vent 74, that allows for bubbles to be removed from the chamber 61. It is typically made of materials, such as Stainless Steel and the like, that are sterilizable. The port 70 of the plate 52, typically centrally positioned therein, interfaces with the fluid coupler 26.

The fluid coupler 26 is stationary, and includes an inlet port 80 for receiving culture medium (along a line 76) from the reservoir 28. Within the axle 40 is a passage 84, terminating in an exit port 86, to which the line 64 is attached for transporting culture medium to the vessel 42. A pump 88, typically a peristaltic pump or the like, typically located along the line 76 between the reservoir 28 and the fluid coupler 26, provides the forces for delivering the culture medium, in the direction of arrows AA, and forms a system or circuit for delivery of culture medium, from the reservoir 28 to the vessel 42 (also in the direction of sub arrows BB), and to the substrate 46. This pumping perfuses the substrate 46 with culture medium, allowing the cells to grow and divide, as detailed herein. Pumping forces are, for example, approximately 1 ml/minute to approximately 3 ml/minute for moving culture medium throughout the bioreactor 22.

The bioreactor 22 can be operated at any temperature or in any environment, for example, ambient or gaseous environments. The specific temperature and environment is dependent on the desired process or the specific cells being used.

In an exemplary operation of the system 20, should the substrate 46 not be fixed in the bioreactor 22, the substrate 46 is coated with a cell adhesive by passing the cell adhesive through it. This is followed by a wash solution of water or phosphate buffered saline. Growing cells are then applied to the substrate 46. The substrate 46 is clamped to the vessel 42 while being held vertically. The bioreactor 22 is then turned to the normal horizontal operating position, and the pump 28 is activated to fill the vessel 42 with culture medium. These substrate 46 preparation procedures are performed under gentle vacuum pressure, such that the flow rate is approximately 1 ml/sec.

Alternately, the substrate 46 can be prepared with adhesive as above, except that the cells have not been added while outside of the bioreactor 22. Here, once the prepared substrate 46 is in the bioreactor 22, cells are introduced to the substrate 46 by pumping cell culture medium into the vessel 42 in a direction opposite of arrows AA. Once the cells are attached, the pump 28 direction is reversed (to the direction of arrows AA) to begin pushing fresh culture medium through the bioreactor 22.

Figure 2:
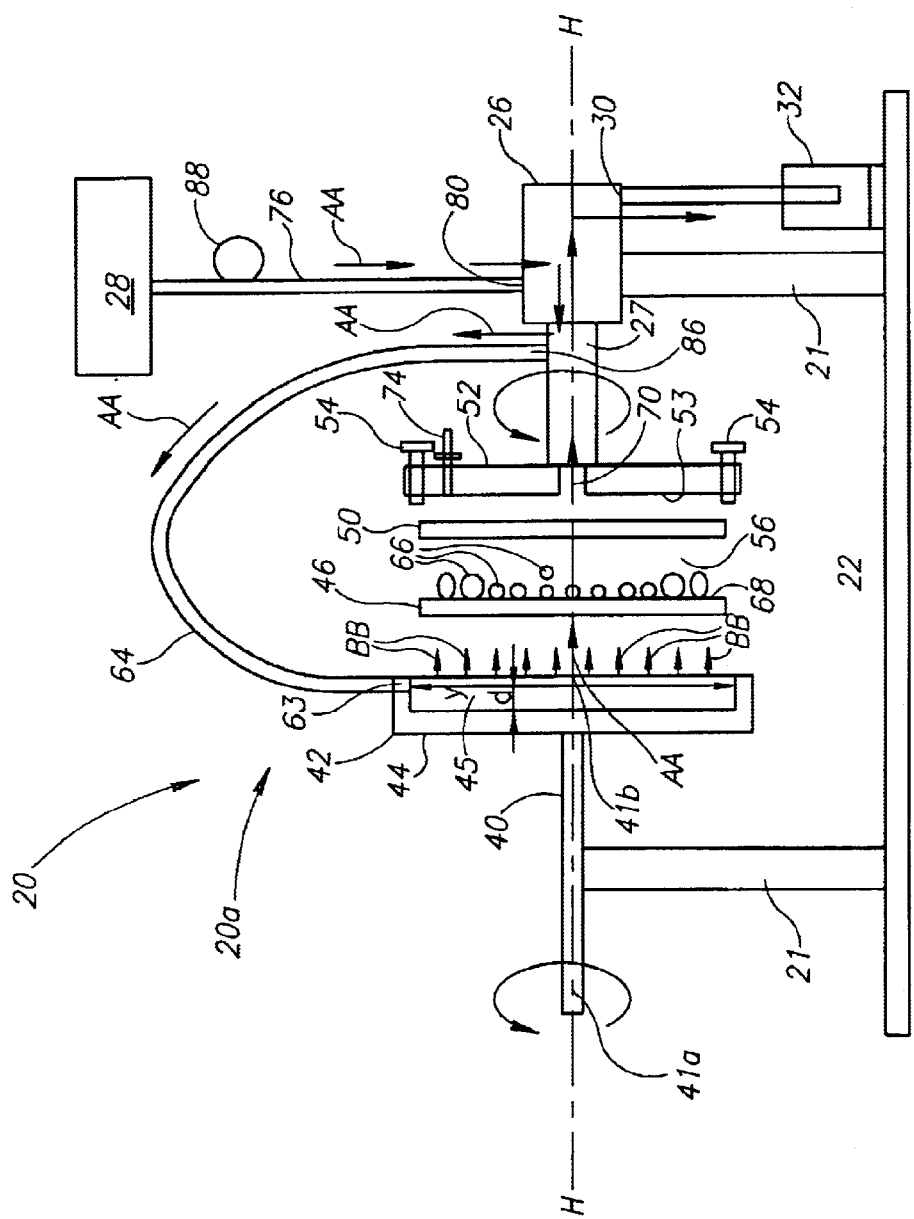
FIG. 2 is a schematic diagram of the embodiment of FIG. 1.

Still alternately, should the substrate 46 be fixed in the bioreactor 22 (the bioreactor 22 closed), adhesive, cells, wash solutions and cell culture medium are introduced to the bioreactor 22 by being pumped therein through the exit port 30 in the fluid coupler 26. This pumping is in reverse to the flow direction described herein (the direction opposite arrows AA of FIG. 2).

In all three situations above, with fresh culture medium being pumped through the bioreactor 22, rotation of the bioreactor 22 now begins. For example, fresh culture medium can be pumped into the culture chamber 45 of the vessel 42, to keep it between approximately one quarter to approximately full during the course of operation, with an approximately half full, or approximately half full to full, culture chamber 45 preferred. The vessel 42 and substrate 46 are rotated, for example, at speeds of approximately 14 rpm. At this same time, culture medium is continuously perfused into the culture chamber 45 of the vessel 42. The rotation of the vessel 42 and substrate 46 coupled with the perfusion of culture medium results in the release of newborn (newly divided) cells, from the mother cells on the substrate 46. These newborn cells are moved in the effluent stream through the exit port 70 in the plate 52 and leave the system 20 through the exit port 30 in the fluid coupler 26, whereby they are collected in the flask 32.

EXAMPLE

Approximately $5 \times 10^7$ L I210 lymphocytic leukemia were attached to a 100 square centimeter nitrocellulose membrane filter coated with Concanavalin A (the substrate) under vacuum at 1 ml/sec. The substrate was now placed into a system having a bioreactor as described above, as the substrate was clamped into the bioreactor. The culture chamber of the vessel was continuously perfused with fresh culture medium, at a flow rate of approximately 2 ml/minute. The bioreactor was rotated at speeds of approximately 14 rpm.

Each division of an attached cell resulted in the release of one newborn daughter cell from the vessel, while the other daughter cell remained attached to the surface of the substrate. Accordingly, the culture vessel maintained a constant cell number, i.e., enabled long-term continuous culture, while releasing $5 \times 10^7$ newborn cells each 10 hour generation time.

The process was continued for many generations, and the released newborn cells grew synchronously through the cell cycle. The cell cycle properties analyzed during rotation include mitotic cycle phase durations, cell sizes and DNA distributions in the cell cycle.

The newborn cells increased in size by approximately ten percent during the first generation (e.g., 10–12 hours) of elution from the culture vessel. During the second generation of growth in the vessel, the newborn cells decreased in size, returning to the initial size at the start of culture in the vessel. From this time forward, the size of the newborn cells released from the bioreactor remained constant. Once the cells adapted to the continuous supply of fresh medium, steady state growth ensued and continued for at least eight generations of growth.

The concentration of released cells remained essentially constant at $7.5 \times 10^4$/min. The released cells were at least 95 percent pure newborn cells, based on their size distributions and G1 content of DNA. The purity of newborn cells released from the vessel was maximal when the vessel was half filled with medium, here, up to the exit port in the flat plate. During subsequent culture, the cells progressed through the cycle normally.

There has been shown and described at least one preferred embodiment of cell culture device and system. It is apparent to those skilled in the art, however, that many changes, variations, modifications, and other uses and applications for the aforementioned device, system and its components are possible, and also such changes, variations, modifications, and other uses and applications which do not depart from the spirit and scope of the invention are deemed to be covered by the invention, which is limited only by the claims which follow.

What is claimed is:

1. An apparatus for producing synchronous cells comprising:
   a) a vessel having a culture chamber with a central axis, configured for receiving culture medium, and closed at one end by a flat plate having an aperture therein located along said central axis of said culture chamber;
   b) a substrate configured for holding cells while allowing said cells to divide, said substrate positioned within said culture chamber substantially parallel to said flat plate and separated from said flat plate by a distance of about 0.2 mm or less;
   c) a system for perfusing said substrate with said culture medium; and,
   d) a mechanism for rotating said substrate along said central axis of said culture chamber;
   wherein culture media received in said vessel traverses a path through said substrate and exits the culture chamber via said aperture in said flat plate.

2. The apparatus of claim 1, additionally comprising:
   a spacer positioned between said substrate and said plate.

3. The apparatus of claim 1, wherein said substrate is non-rigid.

4. The apparatus of claim 1, wherein said substrate is rigid.

5. The apparatus of claim 1, wherein said substrate is configured for holding adhesive for binding with said cells.

6. The apparatus of claim 5, wherein said adhesive is selected from at least one of the group consisting of: charged molecules, lectins and antibodies.

7. The apparatus of claim 6, wherein said charged molecules include poly-D-lysine.

8. The apparatus of claim 6, wherein said lectins include Concanavalin A.

9. The apparatus of claim 5, wherein said adhesive includes fibronectin.

10. The apparatus of claim 1, wherein the substrate is separated from the flat plate by a distance of about 0.1 mm or less.

11. The apparatus of claim 1, wherein the synchronized cells are mammalian cells.

12. The apparatus of claim 11, wherein the mammalian cells are haemopoetic cells.

13. The apparatus of claim 1, wherein said substrate is perfused with said culture medium at a flow rate of at about 3 ml min$^{-1}$ or less.

14. The apparatus of claim 13, wherein said flow rate is about 1 ml min$^{-1}$ or less.

15. The apparatus of claim 1, wherein said mechanism for rotating rotates the substrate between about 10 rpm and about 50 rpm.

16. The apparatus of claim 15, wherein said mechanism for rotating rotates the substrate at about 14 rpm.

17. A method for producing synchronous cells comprising:
   a) contacting a substrate with cells, said substrate configured for holding said cells at least proximate to said substrate while allowing said cells to divide thereby releasing newborn cells;
   b) positioning said substrate
      i) in a vessel having a culture chamber with a central axis, configured for receiving culture medium, and closed at one end by a flat plate having an aperture therein located along said central axis of said culture chamber, and
      ii) substantially parallel to said flat plate and separated from said flat plate by a distance of about 0.2 mm or less;
   c) rotating said substrate;
   d) introducing a culture medium into said vessel whereby said culture medium perfuses through said substrate whereby said newborn cells are suspended in said culture medium prior to passing out of said culture chamber through said aperture; and,
   e) collecting said newborn cells passing out of said aperture for a period sufficient to ensure said collected newborn cells are synchronized.

18. The method of claim 17, wherein said holding cells at least proximate to said substrate includes attaching cells to said substrate.

19. The method of claim 18, wherein said attaching cells to said substrate includes, applying at least one adhesive to said substrate.

20. The method of claim 13, wherein said applying at least one adhesive to said substrate includes: providing at least one adhesive selected from at least one of the group consisting of: charged molecules, lectins and antibodies.

21. The method of claim 20, wherein said charged molecules include poly-D-lysine.

22. The method of claim 20, wherein said lectins include Concanavalin A.

23. The method of claim 19, wherein said applying said at least one adhesive to said substrate includes: providing at least one adhesive including fibronectin.

24. The method of claim 17, wherein said perfusing said substrate is substantially continuous while said substrate is rotating.

25. The method of claim 17, additionally comprising: perfusing said at least one culture medium through said bioreactor before rotating said substrate.

26. The method of claim 17, wherein rotating said substrate is performed at a rate between about 10 rpm and about 50 rpm.

27. The method of claim 26, wherein rotating said substrate is performed at a rate at about 14 rpm.

28. The method of claim 17, wherein the synchronized cells are mammalian cells.

29. The apparatus of claim 28, wherein the mammalian cells are haemopoetic cells.

30. The method of claim 17, wherein said period sufficient to ensure said newborn cells are synchronized is less than about 12 hours.

31. A method for producing synchronous cells comprising:
   a) contacting a substrate with cells, whereby said substrate holds said cells at least proximate to said substrate while allowing said cells to divide thereby releasing newborn cells,
   wherein said substrate is:
      i) positioned in a vessel, having a culture chamber with a central axis, configured for receiving culture medium, and closing at one end by a flat plate having an aperture therein located along said central axis of said culture chamber, and
      ii) located substantially parallel to said flat plate and separated from said flat plate by a distance of about 0.2 mm or less;
   b) rotating said substrate;
   c) introducing a culture medium into said vessel whereby said culture medium perfuses through said substrate suspending said newborn cells in said culture medium prior to passing out of said culture chamber through said aperture; and,
   d) collecting said newborn cells passing out of said aperture for a period sufficient to ensure said collected newborn cells are synchronized.

32. The method of claim 31, wherein said contacting said substrate with cells includes, applying at least one adhesive to said substrate.

33. The method of claim 32, wherein said applying at least one adhesive to said substrate includes: providing at least one adhesive selected from at least one of the group consisting of: charged molecules, lectins and antibodies.

34. The method of claim 33, wherein said charged molecules include poly-D-lysine.

35. The method of claim 33, wherein said lectins include Concanavalin A.

36. The method of claim 32, wherein said applying said at least one adhesive to said substrate includes: providing at least one adhesive including fibronectin.

37. The method of claim 31, wherein rotating said substrate is performed at a rate between about 10 rpm and about 50 rpm.

38. The method of claim 37, wherein rotating said substrate is performed at a rate at about 14 rpm.

39. The method of claim 31, wherein said period sufficient to ensure said newborn cells are synchronized is less than about 12 hours.

40. The method of claim 31, wherein the synchronized cells are mammalian cells.

41. The method of claim 40, wherein the mammalian cells are haemopoetic cells.

42. An apparatus for producing synchronous cells comprising:
   a) a vessel having a culture chamber with a central axis, configured for receiving culture medium, and closed at one end by a flat plate having an aperture therein located along said central axis of said culture chamber;
   b) a substrate configured for holding cells while allowing said cells to divide and release newborn cells, said substrate positioned within said culture chamber substantially parallel to said flat plate and separated from said flat plate by a distance of about 0.2 mm of less;

c) a system for perfusing said substrate with said culture medium;

d) a mechanism for rotating said substrate along said central axis of said culture chamber; and, e) a system for collecting the newborn cells fluidly linked to said culture chamber, wherein culture media received in said vessel traverses a path through said substrate and exits the culture chamber via said aperture in said flat plate.

43. The apparatus of claim 42, additionally comprising:
a spacer, positioned between said substrate and said plate.

44. The apparatus of claim 42, wherein said substrate is non-rigid.

45. The apparatus of claim 42, wherein said substrate is rigid.

46. The apparatus of claim 42, wherein said substrate is configured for holding adhesive for binding with said cells.

47. The apparatus of claim 46, wherein said adhesive is selected from at least one of the group consisting of: charged molecules, lectins and antibodies.

48. The apparatus of claim 47, wherein said charged molecules include poly-D-lysine.

49. The apparatus of claim 47, wherein said lectins include Concanavalin A.

50. The apparatus of claim 46, wherein said adhesive includes fibronectin.

51. The method of claim 42, wherein the substrate is separated from the flat plate by a distance of about 0.1 mm or less.

52. The method of claim 42, wherein said substrate is perfused with said culture medium at a flow rate of at about 3 ml min$^{-1}$ or less.

53. The apparatus of claim 52, wherein said flow rate is about 1 ml min$^{-1}$ or less.

54. The apparatus of claim 42, wherein said mechanism for rotating rotates the substrate between about 10 rpm and about 50 rpm.

55. The apparatus of claim 54, wherein said mechanism for rotating rotates the substrate at about 14 rpm.

56. The apparatus of claim 42, wherein the synchronized cells are mammalian cells.

57. The apparatus of claim 56, wherein the mammalian cells are haemopoetic cells.

* * * * *